United States Patent [19]

Kramer et al.

[11] Patent Number: 4,941,989

[45] Date of Patent: Jul. 17, 1990

[54] CLEANSING AND DISINFECTING COMPOSITIONS

[75] Inventors: David N. Kramer, Stevenson; Philip A. Snow, Henderson, both of Md.

[73] Assignee: Ridgely Products co., Inc., Baltimore, Md.

[21] Appl. No.: 886,171

[22] Filed: Jul. 16, 1986

[51] Int. Cl.$^5$ .............................................. A02D 5/00
[52] U.S. Cl. .................................... 252/102; 252/106; 252/547; 424/446
[58] Field of Search ........................ 252/102, 106, 547

[56] References Cited

U.S. PATENT DOCUMENTS

| | | | |
|---|---|---|---|
| 4,476,108 | 10/1984 | Kessler et al. | 424/50 |
| 4,622,173 | 11/1986 | Broze et al. | 252/547 |
| 4,764,292 | 8/1988 | Sepulveda et al. | 252/547 |

Primary Examiner—Ellis P. Robinson
Assistant Examiner—Leon R. Horne
Attorney, Agent, or Firm—Cushman, Darby & Cushman

[57] ABSTRACT

A cleansing and disinfecting composition comprising an alkaline per-salt and a positively charged phase-transfer agent. The composition preferably also contains a surfactant. The alkaline per-salt is an alkaline water-soluble salt having hydrogen peroxide of crystallization. The positively charged phase-transfer agent is preferably a quaternary ammonium salt. The composition may be formulated as a cream, aa bulk powder, a solution or tablets. It may also be incorporated in wipes, sponges and brushes. The compositions of this invention find utility in health care, as disinfectants in surgical applications, and as decontaminating agents. Specific uses include skin cleansing and disinfecting, treatment for exposure to toxic plants such as poison ivy, treatment for exposure to industrial and agricultural chemicals such as herbicides and pesticides, and cleansing and disinfecting surfaces and sensitive equipment.

34 Claims, 1 Drawing Sheet

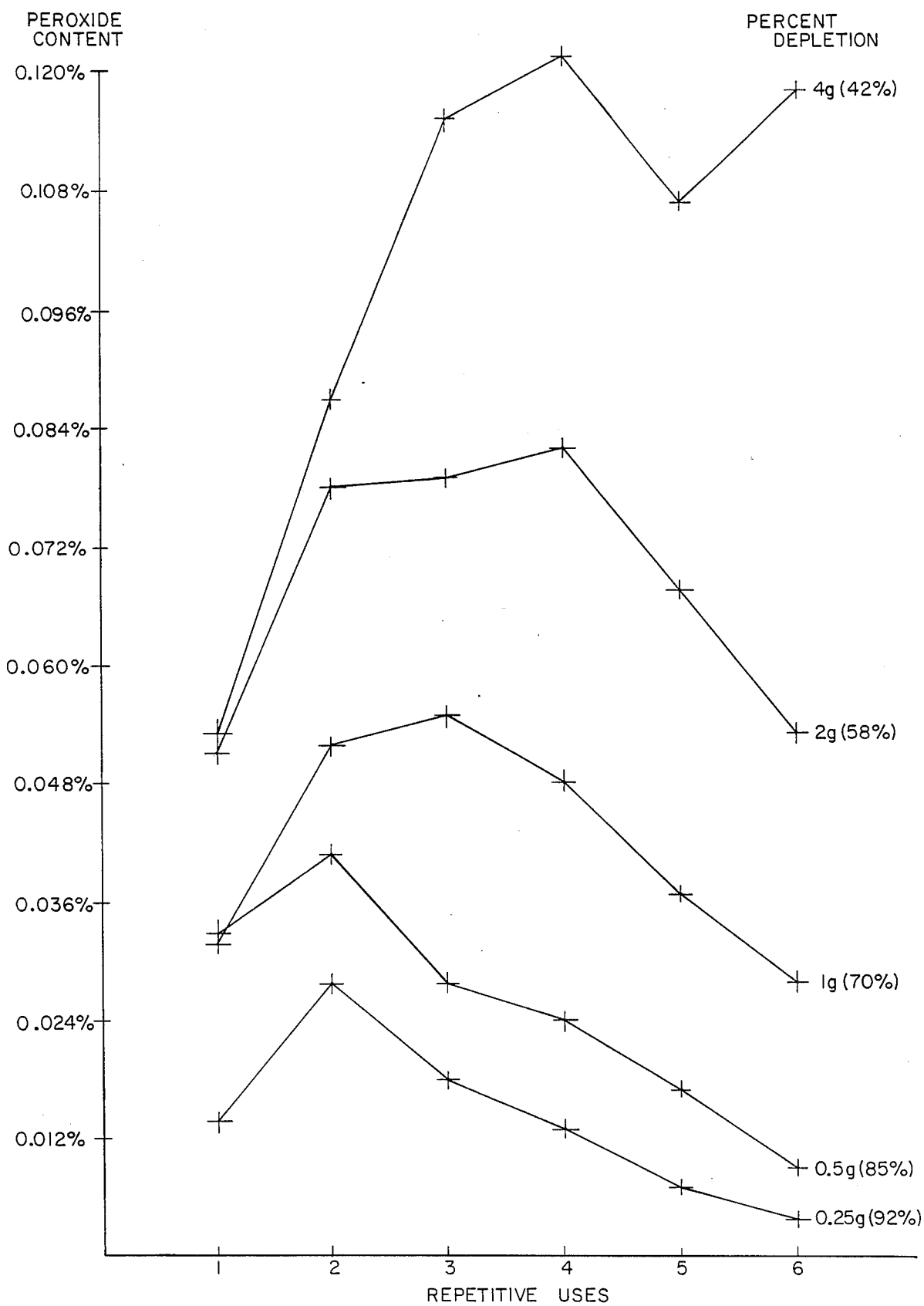

CLEANSING AND DISINFECTING COMPOSITIONS

FIELD OF THE INVENTION

This invention relates to cleansing and disinfecting compositions which find utility in health care, as disinfectants in surgical applications and as decontaminating agents.

BACKGROUND OF THE INVENTION

There is a constant need for cleansing and disinfecting compositions for use in the health care field, as disinfectants in surgical applications and as decontaminating agents. For example, in the health care field there is a need for cleansers and skin exfoliants, antiviral agents, fungicides and bactericides for the treatment and control of such disorders as acne, athlete's foot and dandruff. There is also a need for topical products to give relief to those suffering from insect stings, poison ivy and poison oak. In the surgical field, a need exists for soaps and impregnated sponges for cleansing and disinfecting the skin of surgeons and patients. A need also exists for disinfectant solutions for cleansing and disinfecting the skin as well as for the disinfecting of surgical instruments. Among household and industrial needs are cleansers, algicides for swimming pools, and decontaminating agents for pesticide and chemical spills.

There are many cleansing and disinfecting agents currently in use. However, most of these agents suffer from one or more deficiencies. The deficiencies, one or more of which are exhibited by many currently used cleansing and disinfecting agents, include skin irritation; offensive or irritating odor and inhalation toxicity; corrosiveness toward metal; fabrics and painted surfaces; lack of stability; and low level of efficacy.

SUMMARY OF THE INVENTION

The cleansing and disinfecting compositions of this invention exhibit a number of improvements over prior art compositions. The components of the cleansing and disinfecting compositions of this invention are readily available and relatively inexpensive. The compositions of this invention are not irritating to the skin or absorbed through the skin or mucous membranes. They do not have an offensive or irritating odor and are, in fact, non-volatile. Moreover, the compositions are not corrosive toward metals, fabrics or painted surfaces and are, in many instances, anti-corrosive. In addition, the compositions exhibit a high level of efficacy as rapid cleansing and disinfecting agents and have excellent stability characteristics.

It is therefore an object of this invention to provide improved cleansing and disinfecting compositions.

It is another object of this invention to provide cleansing and disinfecting compositions made from readily available and relatively inexpensive components.

It is still another object of this invention to provide cleansing and disinfecting compositions that are not irritating to the skin.

It is yet another object of this invention to provide cleansing and disinfecting compositions that do not have an offensive or irritating odor.

Another object of this invention is to provide cleansing and disinfecting compositions that are not corrosive toward metals, fabrics or painted surfaces.

Still another object of this invention is to provide highly efficacious and rapid cleansing and disinfecting compositions.

Yet another object of this invention is to provide cleansing and disinfecting compositions having excellent stability characteristics.

The foregoing and other objects are accomplished by the practice of this invention. Broadly, viewed in one of its principal aspects, this invention consists of a cleansing and disinfecting composition comprising an alkaline water-soluble salt having hydrogen peroxide of crystallization and a positively charged phase-transfer agent.

The foregoing cleansing and disinfecting composition may be used in a method to cleanse or disinfect a substrate in need thereof comprising contacting said substrate with an aqueous solution of an alkaline water-soluble salt having hydrogen peroxide of crystallization and a positively charged phase-transfer agent.

The instant invention thus provides cleansing and disinfecting compositions that find utility in health care, as disinfectants in surgical applications and as decontaminating agents. The compositions of this invention are characterized by not being irritating to the skin, by not having an offensive or irritating odor, by not being corrosive, by having excellent stability, and by being rapid and highly effective cleansing and disinfecting agents.

The nature and substance of the present invention as well as its objects and advantages will be more clearly perceived and fully understood by referring to the following description and claims taken in connection with the accompanying drawing which is described briefly below.

BRIEF DESCRIPTION OF THE DRAWING

The drawing is a graph showing the timed release of peroxide from a sponge containing a cleansing composition of the invention which is subjected to a series of water washings.

DESCRIPTION OF THE PREFERRED EMBODIMENTS

The cleansing and disinfecting compositions of this invention are thus characterized by having broad utility, for example, in health care, as disinfectants in surgical applications and as decontaminating agents. The compositions of this invention comprise an alkaline water-soluble salt having hydrogen peroxide of crystallization and a positively charged phase-transfer agent. Depending on the intended use, the compositions of this invention may also contain various additives. For example, the compositions may advantageously contain a surfactant. The compositions may also contain peroxide activators such as enzymes, iodides, and hemin; perfumes such as rose oil; dyes such as fluorescein; emolients such as lanolin and glycol derivatives; gelling agents such as carboxymethyl cellulose; clays such as kaolinite, attapulgite and bentonite; and metal peroxides such as calcium peroxide. Examples of suitable enzymes are horseradish peroxidase, lactoperoxidase and myeloperoxidase.

The compositions of this invention may be compounded in various forms suitable for particular end uses. Thus, the compositions may be formulated as creams, bulk powders, tablets, soaps, and solutions. In addition, they may be incorporated into wipes, sponges and brushes.

The per-salts used in the practice of this invention are alkaline water-soluble salts having hydrogen peroxide of crystalization or forms peroxide upon dissociation. When the salts are dissolved in water, peroxide ion is released. Examples of suitable per-salts are percarbonates, perborates, persilicates and perphosphates associated with a cation that will give an alkaline water-soluble salt. Examples of suitable cations are the alkali metals. Especially preferred is sodium percarbonate having the empirical formula $2Na_2CO_3 \cdot 3H_2O_2$, sodium percarbonate having the hydrogen peroxide of crystallization.

It should be noted that per-salts alone are excellent disinfectants and are superior to hydrogen peroxide in this regard. Hydrogen peroxide is a weak disinfectant and has poor permeability into bacteria. On the other hand, when a per-salt is dissolved in water and liberates hydrogen peroxide, the alkaline salt extracts a proton from the liberated hydrogen peroxide forming the hydroperoxide ion. The hydroperoxide ion, in contrast to hydrogen peroxide, is a strong disinfectant and is readily permeably into bacteria.

The positively charged phase-transfer agent may be a phosphonium salt such as t-butyl phosphonium iodide, a sulfonium salt such as tributyl sulfonium chloride, or a quaternary ammonium salt. The choice of the positively charged phase-transfer agent is critical. The choice of the counter anion of the positively charged phase-transfer agent is not critical in this regard. The hydrocarbyl groups attached to the phosphorous, sulfur or nitrogen must contain a total number of carbons such that the compound is water-soluble but yet has sufficient lipophilic character to permit it to pass from the aqueous phase into a non-polar oil (or organic) phase. The compounds become disinfecting as they become lipophilic.

The preferred positively charged phase-transfer agents are quaternary ammonium salts having a chain of carbon atoms of ca. 6 to 30, and preferably ca. 8 to 25, in length on the quaternary nitrogen. The number of carbons on the nitrogen of the quaternary ammonium salt, as mentioned, is critical. The quaternary ammonium salt must not only be water-soluble but it must also possess sufficient lipophilic character to permit it to pass from the aqueous phase into an oil (or organic) phase. As mentioned above, when the alkaline salt containing hydrogen peroxide of crystallization is dissolved in an aqueous solution of a positively charged phase-transfer agent such as a quaternary ammonium salt, the alkaline salt extracts a proton from the hydrogen peroxide, leaving the negatively charged hydroperoxide ion. The hydroperoxide ion then becomed associated with the quaternary ammonium ion and its negative charge is effectively neutralized:

$$R_4N^+ + O_2H^- \rightarrow [R_4N^+ {}^-O_2H].$$

The resultant lipophilic quaternary ammonium hydroperoxide may then pass from the aqueous phase into an oil, or organic phase where the hydroperoxide ion may exert its disinfecting and decontaminating effects. While quaternary ammonium salts are disinfectants and decontaminants themselves, these properties are enhanced synergistically when they are combined with a per-salt.

U.S. Pat. No. 2,917,428 discloses an aqueous disinfecting composition containing a quaternary ammonium halide, hydrogen peroxide and acetate salts of saturated acyclic amines, which are slightly acidic. Since the aqueous medium must be alkaline, e.g., having a pH equal to or greater than ca. 9.5, before a proton can be extracted from hydrogen peroxide to a significant extent, i.e., approximately half ionized, the compositions in U.S. Pat. No. 2,917,428 cannot form the quaternary ammonium hydroperoxide phase-transfer complex which is critical to the instant invention.

In the practice of this invention, a single positively charged phase-transfer agent or a mixture of positively charged phase-transfer agents may be used. Particularly suitable positively charged phase-transfer agents are didecyl dimethyl ammonium chloride (DDDM), tetradecyl dimethyl benzyl ammonium chloride ("DIBACTOL", manufactured by Huntington Laboratories, Inc.), tetrabutyl ammonium hydrogen sulfate, and mixtures thereof.

While the cleansing and disinfecting compositions of this invention do not require a surfactant, preferred compositions contain one or more surfactants. The surfactant disperses the material to be cleansed or disinfected, thus increasing its surface area and enhancing its contact by the quaternary ammonium hydroperoxide as well as favoring its transfer into a non-polar phase.

The surfactant used in the compositions of this invention may be a nonionic surfactant, an anionic surfactant, a cationic surfactant, or mixtures thereof. Examples of suitable nonionic surfactants are linear alkoxylates such as "TRITON X-100" (manufactured by Rohm and Haas); an alkylphenol ethoxylate such as "ICONOL OP-10" (manufactured by BASF Wyandotte Corp.); and polyoxypropylene-polyoxyethylene block copolymer, such as "PLURONIC F68LF" (manufactured by BASF Wyandotte Corp.). An example of a suitable anionic surfactant is sodium lauryl sulfate. Examples of suitable cationic surfactants are dodecyl ammonium chloride and cetyl dimethyl benzylammonium chloride.

A water-soluble non-volatile, non-flammable glycol ether solvent such as butyl carbitol, may be added in the range of five to forty percent (5%–40%) with optimum at fifteen percent (15%) to assist in dissolving and emulsifying non-polar phases, such as oils and greases.

A preferred composition of this invention contains, in addition to the per-salt, the positively charged phase-transfer agent and the surfactant, a clay or mixture of clays. It has been found that clays spread the material to be decontaminated over a large area, increasing its surface, and they also have the unique property of absorbing and also activating hydrogen peroxide and hydroperoxide ion to form free radicals such as the hydroxy radical and hydroperoxy radical which pass into the oil phase without need for a phase-transfer agent. Preferred clays in the compositions of this invention are kaolinite, attapulgite, bentonite and mixtures thereof.

It has been found that desirable rheological properties are obtained when kaolinite, attapulgite and bentonite are mixed in certain proportions. When water or an aqueous solution, such as an aqueous solution of a per-salt and a positively charged phase-transfer agent, is added to such a mixture of clay, the desired rheological properties are obtained. The mixtures of clay comprise ca. 40% to 85% by weight of kaolinite, ca. 10% to 75% by weight of attapulgite, and ca. 1% to 15% by weight of bentonite. Preferred is a mixture of ca. 50% by weight of kaolinite, ca. 40% by weight of attapulgite and ca. 10% by weight of bentonite. Such mixtures may be mixed with sufficient water or an aqueous solution to give a smooth, creamy composition having an Atterberg Number (plasticity index) within the range of ca.

15 to 75 with an Atterberg Number of ca. 30 being preferred.

The cleansing and disinfecting compositions of this invention broadly contain ca. 10% to 90% by weight of alkaline water-soluble salt containing hydrogen peroxide of crystallization, and preferably ca. 20% to 77% by weight of alkaline water-soluble salt containing hydrogen peroxide of crystallization. The compositions of the invention contain a positively charged phase-transfer agent in the broad range of from a fraction of a percent to ca. 30% by weight, and preferably in the range of ca. 1% to 23% by weight. The amount of surfactant in the compositions of the invention, if a surfactant is present, is broadly within the range of ca. 0.25% to 20% by weight, and preferably within the range of ca. 1% to 15.1% by weight.

A preferred composition of this invention contains, in addition to the alkaline water-soluble salt containing hydrogen peroxide of crystallization, the positively charged phase-transfer agent and the surfactant, a clay or mixture of clays. The amount of clay in the composition may broadly be in the range of ca. 20% to 75% by weight. A preferred range is ca. 35% to 55% by weight of clay.

In addition to the foregoing, the compositions of the invention may contain other additives such as perfumes, dyes, enzymes, metal peroxides and emolients.

Thus, the instant invention provides improved cleansing and disinfecting compositions that are characterized by a number of advantages over cleansing and disinfecting compositions of the prior art. Not only are the compositions of this invention comprised of readily available and relatively inexpensive components, but the compositions are not irritating to the skin or absorbed through the skin or mucous membranes. They do not have an offensive odor and are, in fact, non-volatile. In addition, the compositions are noncorrosive and are, in many instances, anti-corrosive. They also exhibit a high level of efficacy as rapid cleansing and disinfecting agents. Moreover, the compositions have excellent stability.

The cleansing and disinfecting compositions of this invention find utility in health care, as disinfectants in surgical applications and as decontaminating agents. Depending on the intended use and the substrate on which they are to be used, the compositions may be formulated as creams, bulk powders, tablets, soaps, and solutions. The compositions may also be incorporated into wipes, brushes and sponges.

The invention will be more clearly perceived and better understood from the following specific examples.

Example 1

Various cleansing and disinfecting compositions were prepared by combining the following dry and liquid components in various proportions. The dry component was comprised, on a weight basis, of 30% kaolinite, 24% attapulgite, 6% bentonite and 40% sodium percarbonate. The liquid component was an aqueous solution containing 1% by weight of didecyl dimethyl ammonium chloride (DDDM), 0.1% by weight of the linear alkoxylate "TRITON X-100", and 15% by weight of butyl carbitol, a solvent that is miscible with both water and non-polar solvents.

The three clays, kaolinite, attapulgite and bentonite were combined and mixed thoroughly. The sodium percarbonate was blended into the combined clays to form a loose, homogeneous powder. When 2–4 ml. of the liquid component were added to 1 g. of the dry component, a fluid cream with desirable rheologic properties for use with a dispensing mechanism was obtained. For use of non-porous surfaces and for brush application, a ratio of 1 g. of the dry component to 1 ml. of the liquid component is satisfactory. For use on porous materials and on fabrics, as well as for use in squeeze type dispensers, a ratio of 1 g. of the dry component to 4 ml. of the liquid component is preferred.

EXAMPLE 2

A dry component comprising 75.8% by weight of sodium percarbonate, qb 22.7% by weight of tetradecyl dimethyl benzyl ammonium chloride ("DIBACTOL"), and 1.5% by weight of sodium lauryl sulfate was prepared. A cleansing and disinfecting solution was prepared by dissolving 1 part by weight of the foregoing dry component in 15 parts by weight of water. The resulting solution may be applied to the material to be cleansed or disinfected by brushing, spraying or immersion.

EXAMPLE 3

A dry, powdered mixture comprising 77% by weight of sodium percarbonate and 23% by weight of the quaternary ammonium salt "DIBACTOL" was prepared. The powdered mixture was introduced into an absorbent material such as a polyurethane foam, cellulose or cotton, which had been previously impregnated with a 20% by weight solution in isopropanol of the alkylphenol ethoxylate surfactant "ICONOL OP-10". The isopropanol solvent was allowed to evaporate. The resultant pad or sponge was activated by being wet with water and used to scrub or wipe, with occasional rinsing, the area to be cleansed or disinfected.

EXAMPLE 4

Sodium percarbonate was mixed with various liquid components comprising an aqueous solution of a quaternary ammonium salt and a surfactant, and the resultant decontaminating solutions were tested in the decontamination of a toxic chemical in a liquid polymer and a toxic chemical in a chlorinated hydrocarbon solvent. The decontaminating solutions were prepared by dissolving 0.4 g. of sodium percarbonate in 4 ml. of each of the liquid components. The toxic chemical compositions were 0.1 g. of benzene sulfonyl chloride in 10 g. of polymethylmethacrylate and 0.1 g. of "MALATHION" in 10 ml. of chloroform. The following table shows the weight percents of surfactants and quaternary ammonium salts in the various aqueous liquid components. The table also shows the residual activity of the toxic chemical after treatment with the various decontaminating solutions for a period of 5 minutes.

| | Residual Toxic Activity | |
|---|---|---|
| Aqueous Liquid Components | Toxic Chemical in Liquid Polymer | Toxic Chemical in Chlorinated Hydrocarbon |
| 0.1% "TRITON X-100" + 1% DDDM | negligible* | moderate** |
| 0.1% "TRITON X-100" + 15% butyl carbitol | negligible | negligible |
| 0.1% "TRITON X-100" + 1% "DIBACTOL" | negligible | moderate |
| 0.1% "TRITON"x-100 + | negligible | negligible. |

-continued

| Aqueous Liquid Components | Residual Toxic Activity | |
|---|---|---|
| | Toxic Chemical in Liquid Polymer | Toxic Chemical in Chlorinated Hydrocarbon |
| 15% butyl carbitol | | |

*negligible: 1 g.
**moderate: 5 g.

The foregoing data illustrate the efficacy of the compositions of this invention as decontaminating agents for toxic chemicals.

EXAMPLE 5

The dry component of Example 1 was mixed with the same liquid components shown in Example 4, and the resultant compositions were tested in the decontamination of a toxic chemical in a liquid polymer and a toxic chemical in a chlorinated hydrocarbon solvent. The decontaminating compositions were prepared by mixing 1 g. of the dry component with 4 ml. of each of the liquid components. The toxic chemical compositions in liquid polymer and in chlorinated hydrocarbon were the same as those described in Example 4. The following table shows the weight percents of surfactants and quaternary ammonium salts in the various aqueous liquid components. The table also shows the residual activity of the toxic chemical after treatment with the various decontaminating compositions for a period of 5 minutes.

| Aqueous Liquid Components | Residual Toxic Activity | |
|---|---|---|
| | Toxic Chemical in Liquid Polymer | Toxic Chemical in Chlorinated Hydrocarbon |
| 0.1% "TRITON X-100" + 1% DDDM | negligible* | negligible |
| 0.1% "TRITON X-100" + 15% butyl carbitol | negligible | negligible |
| 0.1% "TRITON X-100" + 1% "DIBACTOL" | negligible | negligible |
| 0.1% "TRITON X-100" + 15% butyl carbitol | negligible | negligible. |

*negligible: 1 μg.

The foregoing illustrates the efficacy of the clay-containing compositions of this invention as decontaminating agents for toxic chemicals.

EXAMPLE 6

A cleansing and disinfecting composition according to this invention was prepared by combining the following dry component and liquid component. The dry component was prepared by mixing 30% by weight of kaolinite, 24% by weight of attapulgite, 6% by weight of bentonite, 30% by weight of sodium percarbonate and 10% by weight of calcium peroxide. The liquid component was an aqueous solution containing 1% by weight of DDDM and 0.1% by weight of "TRITON X-100".

A 50% by weight solution of the pesticide "MALATHION" in xylene was diluted with xylene and placed on watch glasses so as to cover two one-inch square surfaces. Evaporation of the xylene left a 50 mg. residue of "MALATHION" on each watch glass. In triplicate runs, a slurry of 1 g. of the above dry component in 3 ml. of the above liquid component was brushed onto the watch glass and left in place for 5 minutes. Each of the three samples was then extracted with chloroform.

The cholinesterase test described by Kramer and Gamson in *Anal. Chem.*, 30, 251 (1958) was used to test for the presence of "MALATHION". A blank consisting of a xylene/chloroform solution was placed on the enzyme strip to ensure that there were no interfering substances in either solvent. The xylene solution of "MALATHION" that was placed on the watch glasses was placed on an enzyme strip and gave a positive test, i.e., the enzyme was inhibited. The three chloroform extracts from the treated watch glasses were placed on enzyme strips and, in each case, the enzyme was not inhibited. This indicates that, not only was the "MALATHION" decontaminated by the cleansing composition, but the oxidation products of "MALATHION" were not inhibitory to the enzyme.

EXAMPLE 7

Sodium percarbonate solutions of various concentrations were prepared by dissolving varying quantities of sodium percarbonate in water. Cultures of Streptococcus faecalis were treated for 10 and 20 minutes with these solutions at 25° C. and 40° C., and the percent reduction in bacteria was determined in each case. The results are shown in the following table.

| Sodium Percarbonate in Solution (ppm) | $H_2O_2$ in Solution (m. mol.) | Temp. °C. | % Reduction in Bacteria | |
|---|---|---|---|---|
| | | | 10 min. | 20 min. |
| 0 ppm | 0 m. mol. | 25° C. | 64.8% | 53.6% |
| 379 ppm | 3.1 m. mol. | 25° C. | 69.6% | 98.8% |
| 758 ppm | 6.2 m. mol. | 25° C. | 84.3% | 99.9999% |
| 1515 ppm | 12.5 m. mol. | 25° C. | 99.1% | 99.9999% |
| 758 ppm | 6.2 m. mol. | 40° C. | 99.9999% | 99.9999% |

The above data show that an aqueous solution of the per-salt sodium percarbonate is an effective disinfectant whose effectiveness is enhanced by increased contact time, elevated temperature and increased sodium percarbonate concentration.

EXAMPLE 8

Polyurethane surgical scrub brushes (2 in.×3 in.×1 in.) were prepared by forming interior pockets and inserting varying amounts of the powdered mixture of Example 3. After the powdered mixture was added, the incisions in the sponges were sealed with plastic adhesive. Both sides of each sponge were then impregnated with 1 ml. of a 20% by weight solution of "ICONOL OP-10" in isoproponol. The isopropanol solvent was then allowed to evaporate. The peroxide content was measured on six sequential water washings of 60 ml. each over a 10 minute period, mimicking a standard pre-operative scrub procedure. Each 60 ml. washing was collected and the peroxide content determined by permanganate titration. The results, illustrated in the drawing, indicate a timed release of peroxide by the dissolution of the sodium percarbonate. The treated surgical scrub sponges are seen to provide effective anti-microbial peroxide activity with repeated washing.

EXAMPLE 9

The dry component of Example 1 was mixed with aqueous solutions containing varying amounts of a quaternary ammonium salt phase-transfer agent and the resultant decontaminating compositions were used to treat various substrates contaminated with benzene sulfonyl chloride. In each case, 1.0 g. of the dry component of Example 1 was mixed with 1.0 ml. of an aqueous solution of the phase-transfer agent and the resultant decontaminating composition brought into contact with the substrate for 10 minutes. The following table gives the phase-transfer agent used, its concentration in the original aqueous solution, the substrate treated and the residual toxic contaminant on the substrate after treatment.

| Phase Transfer Agent | Concentration (ppm) | Substrate Chloroform | Cloth | Greasy Cloth |
|---|---|---|---|---|
| DDDM | 10,000 | negligible | negligible | negligible |
| " | 1,000 | very weak | negligible | negligible |
| " | 100 | very weak | negligible | negligible |
| " | 10 | strong | negligible | negligible |
| Tetrabutyl Ammonium Hydrogen Sulfate | 10,000 | negligible | negligible | very weak |
| Tetrabutyl Ammonium Hydrogen Sulfate | 1,000 | weak | negligible | very weak |
| Tetrabutyl Ammonium Hydrogen Sulfate | 100 | moderate | negligible | very weak |
| Tetrabutyl Ammonium Hydrogen | 10 | strong | very weak | very weak | wherein, negligible 1 μg.
very weak ca. 1-2 μg.
weak ca. 2-3 μg.
moderate ca. 3-5 μg.
strong 5 μg.

The foregoing data illustrate the effectiveness of the decontaminating compositions of this invention against toxic chemicals in various substrates.

Thus, the instant invention provides cleansing and disinfecting compositions that find utility in health care, as disinfectants in surgical applications and as decontaminating agents. The compositions of the invention are characterized by not being irritating to the skin, by not having an offensive or irritating odor, by not being corrosive, by having excellent stability, and by being highly effective cleansing and disinfecting agents.

Depending on the end use, the compositions of the invention may be compounded in various forms. For example, they may be used as bulk powders or compressed into tablets. The compositions may also be incorporated into soaps. The components of the compositions may be mixed with a liquid such as water or an alcohol to form a cleansing and disinfecting cream or solution.

While specific embodiments of the present invention have been shown and described in detail to illustrate the inventive principles, it is to be understood that such showing and description have been offered only by way of example and not by way of limitation. Protection by Letters Patent of this invention in all its aspects as the same are set forth in the appended claims is sought to the broadest extent that the prior art allows

What is claimed is:

1. A cleansing and disinfecting composition comprising from about 10% to about 90% by weight of an alkaline water-soluble salt having hydrogen peroxide of crystallization and from about a fraction of a percent to about 30% by weight of a positively charged phase-transfer agent, including either a phosphonium salt, a sulfonium salt, or a quaternary ammonium salt having a chain of carbon atoms on the quaternary nitrogen approximately 6 to 30 atoms in length.

2. A cleansing and disinfecting composition comprising from about 10% to about 90% by weight of an alkaline water-soluble salt having hydrogen peroxide of crystallization, from about a fraction of a percent to about 30% by weight of a positively charged phase-transfer agent and from about 1% to about 20% by weight of a non-liquid surfactant.

3. The cleansing and disinfecting composition of claim 2 wherein said alkaline water-soluble salt having hydrogen peroxide of crystallization or forming peroxide upon dissociation is selected from the group consisting of percarbonates, persilicates, perborates and perpyrophosphates.

4. The cleansing and disinfecting composition of claim 3 wherein said positively charged phase-transfer agent is selected from the group consisting of quaternary ammonium salts, phosphonium salts and sulfonium salts.

5. The cleansing and disinfecting composition of claim 4 wherein the surfactant is selected from the group consisting of anionic surfactants, cationic surfactants, nonionic surfactants, and mixtures thereof.

6. The cleansing and disinfecting composition of claim 5 wherein said alkaline water-soluble salt having hydrogen peroxide of crystallization is sodium percarbonate.

7. The cleansing and disinfecting composition of claim 6 wherein said positively charged phase-transfer agent is a quaternary ammonium salt having a chain of carbon atoms of ca. 6 to 30 in length on the quaternary nitrogen.

8. The cleansing and disinfecting composition of claim 7 wherein said quaternary ammonium salt has a chain of carbon atoms of approximately 8 to 25 in length on the quaternary nitrogen.

9. The cleansing and disinfecting composition of claim 8 wherein said composition contains approximately 10% to 90% by weight of sodium percarbonate, a fraction of a percent to approximately 30% by weight of quaternary ammonium salt, and approximately 1% to 20% by weight of surfactant.

10. The cleansing and disinfecting composition of claim 9 wherein said composition contains approximately 20% to 77% by weight of sodium percarbonate, approximately 1% to 23% by weight of said quaternary ammonium salt, and approximately 1.0% to 15.1% of said surfactant.

11. The cleansing and disinfecting composition of claim 10 wherein the surfactant is selected from the group consisting of a linear alkoxylate, an alkylphenol ethoxylate, sodium lauryl sulfate, and mixtures thereof.

12. The cleansing and disinfecting composition of claim 11 wherein said quaternary ammonium salt is selected from the group consisting of didecyl dimethyl ammonium chloride, tetradecyl dimethyl benzyl ammonium chloride, tetrabutyl ammonium hydrogen sulfate and mixtures thereof.

13. The cleansing and disinfecting composition of claim 12 wherein said composition is in an aqueous solution.

14. A cleansing and disinfecting composition comprising from about 10% to about 90% by weight of an alkaline water-soluble salt having hydrogen peroxide of crystallization, from about a fraction of a percent to about 30% by weight of a positively charged phase-transfer agent, including either a phosphonium salt, a sulfonium salt, or a quaternary ammonium salt having a chain of carbon atoms on the quaternary nitrogen approximately 6 to 30 atoms in length, from about 1% to about 20% by weight of a surfactant and from about 20% to about 75% by weight of a clay.

15. The cleansing and disinfecting composition of claim 14 wherein said clay is selected from the group consisting of kaolinite, attapulgite, bentonite and mixtures thereof.

16. The cleansing and disinfecting composition of claim 15 which in addition contains an alkaline earth metal peroxide.

17. The cleansing and disinfecting composition of claim 8 which in addition contains an enzyme which activates peroxide selected from the group consisting of horseradish peroxidase, lactoperoxidase, myeloperoxidase and mixtures thereof.

18. A cleansing and disinfecting composition prepared by mixing approximately 1 part by weight of a dry component consisting of approximately 30% by weight of kaolinite, approximately 24% by weight of attapulgite, approximately 6% by weight of bentonite and approximately 40% by weight of sodium percarbonate with approximately 1 to approximately 4 parts by weight of an aqueous solution containing approximately 1% by weight of didecyl dimethyl ammonium chloride, approximately 0.1% by weight of a linear alkoxylate and approximately 15% by weight of butyl carbitol, the resulting solution having a pH of at least 9.5.

19. A cleansing and disinfecting composition prepared by mixing approximately 1 part by weight of a dry component consisting of approximately 30% by weight of kaolinite, approximately 24% by weight of attapulgite, approximately 6% by weight of bentonite, approximately 30% by weight of sodium percarbonate and approximately 10% by weight of calcium peroxide with approximately 1 to 4 parts by weight of an aqueous solution containing approximately 1% by weight of didecyl dimethyl ammonium chloride, approximately 0.1% by weight of a linear alkoxylate and approximately 15% by weight of butyl carbitol, the resulting solution having a pH of at least 9.5.

20. A cleansing and disinfecting composition comprising: from about 10% to about 90% by weight of an alkaline water-soluble salt having hydrogen peroxide of crystallization or forming a negative ion peroxide species upon dissociation; from about 1% to about 20% by weight of a surfactant; from about a fraction of a percent to about 30% by weight of a positively charged compound which, when the composition is added to water, said positively charged compound reacts with said negative ion peroxide species forming an ion pair such that said ion pair is rendered soluble in a phase in which said negative ion peroxide species was insoluble prior to formation of said ion pair; said alkaline water-soluble salt having hydrogen peroxide of crystallization or forming said negative ion species upon dissociation is selected from the group consisting of percarbonates, persilicates, perborates and perpyrophosphates; and surfactant is selected from the group consisting of anionic surfactants, cationic surfactants, nonionic surfactants, and mixtures thereof; and said positively charged compound is selected from the group consisting of quaternary ammonium salts, phosphonium salts and sulfonium salts; the aqueous solution of said composition having a pH of at least 9.5.

21. The cleansing and disinfecting composition of claim 20, wherein said alkaline water-soluble salt having hydrogen peroxide of crystallization is sodium percarbonate.

22. The cleansing and disinfecting composition of claim 21, wherein said positively charged compound is a quaternary ammonium salt having a chain of carbon atoms of approximately 6 to 30 in length on the quaternary nitrogen.

23. The cleansing and disinfecting composition of claim 22, wherein said quaternary ammonium salt has a chain of carbon atoms of approximately 8 to 25 in length on the quaternary nitrogen.

24. The cleansing and disinfecting composition of claim 22, wherein said composition contains from about 20% to about 77% by weight of said sodium percarbonate, from about 1% to about 23% by weight of said quaternary ammonium salt, and from about 1.0% to about 15.1% of said surfactant.

25. The cleansing and disinfecting composition of claim 24, wherein the surfactant is selected from the group consisting of a linear alkoxylate, an alkylphenol ethoxylate, sodium lauryl sulfate, and mixtures thereof.

26. The cleansing and disinfecting composition of claim 24, wherein said quaternary ammonium salt is selected from the group consisting of didecyl dimethyl ammonium chloride, tetradecyl dimethyl benzyl ammonium chloride, tetrabutyl ammonium hydrogen sulfate and mixtures thereof.

27. A cleansing and disinfecting composition comprising:
a dry component which is activated when mixed with water, the dry component comprising from about 10% to about 90% by weight of an alkaline water-soluble salt having hydrogen peroxide of crystallization, from about a fraction of a percent to about 30% by weight of a positively charged compound, including either a phosphonium salt, a sulfonium salt, or a quaternary ammonium salt having a chain of carbon atoms on the quaternary nitrogen approximately 6 to 30 atoms in length, and from about 1% to about 20% by weight of a surfactant;
approximately 1 part by weight of the dry component being dissolved in approximately 15 parts by weight of water such that the alkaline water-soluble salt forms a negatively charged hydroperoxide ion; and
the hydroperoxide ion reacting with the positively charged compound to form an active hydroperoxide.

28. The composition of claim 27, wherein the aqueous solution has a pH of at least 9.5.

29. The cleansing and disinfecting composition of claim 27, wherein said alkaline water-soluble salt having hydrogen peroxide of crystallization is sodium percarbonate.

30. The cleansing and disinfecting composition of claim 29, wherein said positively charged compound is a quaternary ammonium salt having a chain of carbon atoms of approximately 6 to 30 in length on the quaternary nitrogen.

31. The cleansing and disinfecting composition of claim 30, wherein said quaternary ammonium salt has a chain of carbon atoms of approximately 8 to 25 in length on the quaternary nitrogen.

32. The cleansing and disinfecting composition of claim 30, wherein said composition contains from about 20% to about 77% by weight of said sodium percarbonate, from about 1% to about 23% by weight of said quaternary ammonium salt, and from about 1.0% to about 15.1% of said surfactant.

33. The cleansing and disinfecting composition of claim 30, wherein said quaternary ammonium salt is selected from the group consisting of didecyl dimethyl ammonium chloride, tetradecyl dimethyl benzyl ammonium chloride, tetrabutyl ammonium hydrogen sulfate and mixtures thereof.

34. The cleansing and disinfecting composition of claim 27, wherein the surfactant is selected from the group consisting of a linear alkoxylate, an alkylphenol ethoxylate, sodium lauryl sulfate, and mixtures thereof.

* * * * *